United States Patent
Tomonaga et al.

[11] Patent Number: 6,088,629
[45] Date of Patent: Jul. 11, 2000

[54] DISPLAYING METHOD OF REACTION PATH DIAGRAM OF COMPOUND

[75] Inventors: Atsushi Tomonaga, Musashino; Fumio Tamura, Inashiki-gun, both of Japan

[73] Assignee: Kureha Kagaku Kogyo Kabushiki Kaisha, Tokyo, Japan

[21] Appl. No.: 09/068,595

[22] PCT Filed: Nov. 14, 1996

[86] PCT No.: PCT/JP96/03345
§ 371 Date: May 11, 1998
§ 102(e) Date: May 11, 1998

[87] PCT Pub. No.: WO97/18517
PCT Pub. Date: May 22, 1997

[30] Foreign Application Priority Data

Nov. 15, 1995 [JP] Japan .................................. 7-296852

[51] Int. Cl.$^7$ .................................................. G05B 21/00
[52] U.S. Cl. ........................................... 700/266; 345/965
[58] Field of Search .................................. 700/83, 84, 85, 700/90, 266; 707/526; 345/965, 968

[56] References Cited

U.S. PATENT DOCUMENTS

| | | | |
|---|---|---|---|
| 5,337,405 | 8/1994 | Lindauer et al. ...................... | 395/147 |
| 5,397,697 | 3/1995 | Lam et al. .................................. | 435/6 |
| 5,527,674 | 6/1996 | Guerra et al. .............................. | 435/6 |
| 5,700,928 | 12/1997 | Hodgson et al. ...................... | 536/23.7 |

FOREIGN PATENT DOCUMENTS 01085131   3/1989   European Pat. Off. .

OTHER PUBLICATIONS

Hidetoshi Tanaka, "Metabolic Reaction Database," 1990, IPSJ Research Report, vol. 90, No. 63, (DBS78–14) pp. 129–137.

Hopkinson et al., "Chemical Reaction Sequence Searching," 1993, Chemical Structures 2, pp. 459–468.

Hamm et al., "Generalization and Representation of Synthesis Pathways in the COSYMA System," 1992, Recl. Trav. Chim. Pays–Bas, vol. 111, No. 6, pp. 317–322.

Peter D. Karp et al., "Representing, Analyzing, and Synthesizing Biochemical Pathways", Apr. 1994, IEEE Expert, vol. 9, No. 2, pp. 11–21.

*Primary Examiner*—Joseph E. Palys
*Assistant Examiner*—Nitin Patel
*Attorney, Agent, or Firm*—Beyer Weaver & Thomas, LLP

[57] ABSTRACT

A method for displaying a reaction path diagram of compound by use of an apparatus comprising an input device, display device, and a storage device, the displaying method of reaction path diagram of compound comprising: a step of preparing a reaction path diagram based on input data and displaying the reaction path diagram on the display device; a step of extracting an end compound accompanied by an undisplayed, adjacent reaction from compounds constituting the reaction path diagram and displaying a guide mark corresponding to the undisplayed, adjacent reaction on the display device; and a step of scrolling the reaction path diagram so as to display an undisplayed compound that makes the undisplayed, adjacent reaction indicated by the selected guide mark, on the display device.

11 Claims, 20 Drawing Sheets

Fig.3

COMPOUND INFO FILE
                                                                21

| COMPOUND NUMBER | CANONICAL DATA | REFERENCE DATA |
|---|---|---|
| $C_1$ | 1%2% ............... | NAME,LITERATURE, PHYSICAL PROPERTIES,ETC. |
| $C_2$ | ............... | |
| $C_3$ | ............... | |
| $C_4$ | ............... | |
| $C_5$ | ............... | |
| $C_6$ | ............... | |
| $C_7$ | ............... | |

Fig.4

ENZYME INFO FILE

| ENZYME NUMBER | (SUBSTRATE) COMPOUND NUMBER | (PRODUCT) COMPOUND NUMBER | REFERENCE DATA |
|---|---|---|---|
| $E_1$ | $C_1$ | $C_2$ | NAME, LITERATURE, PHYSICAL PROPERTIES, ETC. |
| $E_2$ | $C_2$ | $C_3$ | |
| $E_3$ | $C_3$ | $C_4$ | |
| $E_4$ | $C_3$ | $C_6$ | |
| $E_5$ | $C_5$ | $C_6$ | |
| $E_6$ | $C_6$ | $C_7$ | |

Fig.5

RELATION INFO FILE 23

| COMPOUND NUMBER | (SUBSTRATE) ENZYME NUMBER | (PRODUCT) ENZYME NUMBER | (INHIBITOR) ENZYME NUMBER |
|---|---|---|---|
| $C_1$ | $E_1$ | | |
| $C_2$ | $E_2$ | $E_1$ | |
| $C_3$ | $E_3, E_4$ | $E_2$ | |
| $C_4$ | | $E_3$ | |
| $C_5$ | $E_5$ | | |
| $C_6$ | $E_6$ | $E_5$ | $E_4$ |
| $C_7$ | | $E_6$ | |

IMAGE DATA 80a (MOLECULAR STRUCTURE DIAGRAM)

Fig.6B

BOND TABLE DATA 81a

| NUMBER OF ATOMS | NUMBER OF BONDS |
|---|---|
| 7 | 7 |

| NUMBER OF ATOM | X-COORDINATE | Y-COORDINATE | Z-COORDINATE | ELEMENT NAME | CHARGE | MASS | BONDING ATOM PAIR | | TYPE OF BOND | UP/DOWN |
|---|---|---|---|---|---|---|---|---|---|---|
| 1 | 3.0386 | -2.4082 | 0.0000 | C | 0 | 0 | 1 | 2 | 2 | 0 |
| 2 | 3.0386 | -0.9082 | 0.0000 | C | 0 | 0 | 2 | 3 | 1 | 0 |
| 3 | 1.7396 | -0.1582 | 0.0000 | C | 0 | 0 | 3 | 4 | 2 | 0 |
| 4 | 0.4405 | -0.9082 | 0.0000 | N | 0 | 0 | 4 | 5 | 1 | 0 |
| 5 | 0.4405 | -2.4082 | 0.0000 | C | 0 | 0 | 5 | 6 | 2 | 0 |
| 6 | 1.7396 | -3.1582 | 0.0000 | C | 0 | 0 | 6 | 1 | 1 | 0 |
| 7 | 4.3376 | -3.1582 | 0.0000 | C | 0 | 0 | 1 | 7 | 1 | 0 |

Fig.6C

CANONICAL DATA 82a

1%1%1-2%3%5%N/6%7/

IMAGE DATA 80b (MOLECULAR STRUCTURE DIAGRAM)

Fig.7B

BOND TABLE DATA 81b

| NUMBER OF ATOMS | NUMBER OF BONDS |
|---|---|
| 7 | 7 |

| NUMBER OF ATOM | X-COORDINATE | Y-COORDINATE | Z-COORDINATE | ELEMENT NAME | CHARGE | MASS | BONDING ATOM PAIR | | TYPE OF BOND | UP/DOWN |
|---|---|---|---|---|---|---|---|---|---|---|
| 1 | 3.5200 | -4.7362 | 0.0000 | C | 0 | 0 | 1 | 2 | 1 | 0 |
| 2 | 3.5514 | -3.2366 | 0.0000 | C | 0 | 0 | 2 | 3 | 1 | 0 |
| 3 | 4.8659 | -2.5139 | 0.0000 | C | 0 | 0 | 3 | 4 | 2 | 0 |
| 4 | 4.8973 | -1.0143 | 0.0000 | C | 0 | 0 | 2 | 5 | 2 | 0 |
| 5 | 2.2684 | -2.4595 | 0.0000 | C | 0 | 0 | 5 | 6 | 1 | 0 |
| 6 | 2.2998 | -0.9599 | 0.0000 | C | 0 | 0 | 4 | 7 | 1 | 0 |
| 7 | 3.6143 | -0.2372 | 0.0000 | N | 0 | 0 | 7 | 6 | 2 | 0 |

Fig.7C

CANONICAL DATA 82b

1%1%1-2%3%65%N/6%7/

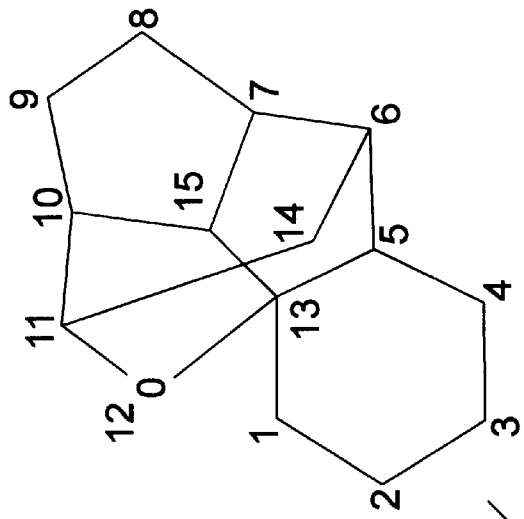
Fig.8B
IMAGE DATA 80d
(MOLECULAR STRUCTURE DIAGRAM)
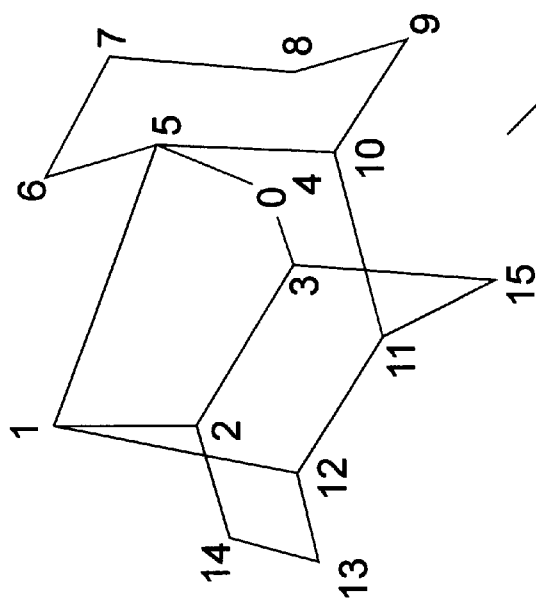
Fig.8A
IMAGE DATA 80c
(MOLECULAR STRUCTURE DIAGRAM)
Fig.8C
CANONICAL DATA 82c
1—1—1—O1—2—2—3—3—4—5—6—7—8—9—/6—8/7—
10/10—14/11—15/12—13/

DISPLAYING METHOD OF REACTION PATH DIAGRAM OF COMPOUND

TECHNICAL FIELD

The present invention relates to a displaying method of reaction path diagram of compound for displaying a reaction path diagram of compound on a display.

BACKGROUND ART

There are conventional database systems that can display a chemical reaction scheme (formula) of compound on the display. The database systems store data of chemical formulas of existing compounds and display on the display a chemical reaction scheme of one step including a compound as a starting material and a compound as a product, the compounds being obtained by search of the data. Examples of the database systems include the integrated chemical information control system "ISIS" and the reaction information control system "REACCS" available from MDL Inc., Co., the United States.

However, when a compound changed step by step through a plurality of chemical reactions, the conventional database systems were not able to display the series of chemical reactions. It was, therefore, not possible to efficiently search for a path along which a compound changed step by step through a plurality of chemical reactions.

An object of the present invention is to provide a displaying method of reaction path diagram of compound for efficiently searching for a reaction path of compound, thus solving the above problem.

DISCLOSURE OF THE INVENTION

A displaying method of reaction path diagram of compound according to the present invention is a method for displaying a reaction path diagram of compound by use of an apparatus comprising input means, display means, and storage means storing at least reaction path information about compounds in the form of a reaction path information file, said displaying method of reaction path diagram of compound comprising;

a step of searching said reaction path information file, based on data accepted by said input means, to prepare a reaction path diagram having a first predetermined number of reaction steps, and displaying said reaction path diagram on said display means, a step of extracting every end compound that is located at the end of the diagram, from compounds constituting the reaction path diagram displayed on said displaying means, searching said reaction path information file to extract an end compound accompanied by an undisplayed, adjacent reaction that is an adjacent reaction thereto and is not displayed on said display means, from said every end compound, and displaying on said display means a guide mark corresponding to the undisplayed, adjacent reaction in relation to the end compound accompanied by the undisplayed, adjacent reaction, and a step of, when said guide mark is selected, searching said reaction path information file for an undisplayed compound that makes the undisplayed, adjacent reaction indicated by the selected guide mark and is not displayed on said display means, and scrolling the reaction path diagram displayed on said display means so as to display said undisplayed compound on said display means.

In the displaying method of reaction path diagram of compound of the present invention stated above, said step of scrolling the reaction path diagram may further comprise a step of obtaining a number of reaction steps from the end compound with respect to said end compound corresponding to said selected guide mark, for each of the compounds constituting the reaction path diagram displayed on said display means, and extracting a compound whose number of reaction steps obtained is not more than a second predetermined number of reaction steps. In this case, it is preferable that, when scrolling said reaction path diagram, said undisplayed compound be displayed on said display while displaying said extracted compound on the display means.

Further, in the displaying method of reaction path diagram of compound of the present invention, the reaction path information file may be prepared based on data accepted by said input means. Namely, another displaying method of reaction path diagram of compound of the present invention is a method for displaying a reaction path diagram of compound by use of an apparatus comprising input means, display means, and storage means;

wherein said storage means comprises a compound information file storing a list indicating a relation between numbers of compounds and canonical data corresponding to the respective compounds, and additional information about said compounds, an enzyme information file storing a list indicating a relation among enzyme numbers of enzymes, compound numbers of compounds being substrates for said enzymes, and compound numbers of compounds being products by said enzymes, and additional information about said enzymes, and a relation (correlation) information file storing a list indicating a relation among compound numbers of compounds as keys, enzyme numbers of enzymes for which said compounds are substrates, and enzyme numbers of enzymes from which said compounds are products;

said displaying method of reaction path diagram of compound comprising;

a step of, when said input means accepts data about a compound, preparing said canonical data uniquely indicating a chemical structure of said compound from the data, further searching said compound information file, based on the canonical data, and thereby reading a compound number of the compound corresponding to said canonical data if said canonical data exists in said compound information file, a step of reading an enzyme number of an enzyme for which the compound is a substrate and an enzyme number of an enzyme by which the compound is a product out of said relation information file, based on the compound number of the compound read in the foregoing step, a step of reading a compound number of a compound being a substrate for the enzyme and a compound number of a compound being a product by the enzyme out of said enzyme information file, based on the enzyme number of each of the enzymes read in the preceding step, a step of storing the compound numbers of the compounds and the enzyme numbers of the enzymes read in the foregoing steps, in said storage means in the form of a reaction path information file, a step of repeating the foregoing steps to prepare a reaction path diagram having a first predetermined number of reaction steps and displaying said reaction path diagram on said display means, a step of extracting every end compound that is located at the end of the diagram, from compounds constituting the reaction path diagram displayed on said display means, searching said reaction path information file to extract an end compound accompanied by an undisplayed, adjacent reaction that is an adjacent reaction thereto and is not displayed on said display means from said every end compound, and displaying on said display means a guide mark corresponding to the undisplayed, adjacent reaction in relation to the end compound accompanied by the undisplayed, adjacent reaction, and a step of, when the guide mark is selected, searching said reaction path information file for an undisplayed compound that makes the undisplayed, adjacent reaction indicated by the selected guide mark and is not displayed on said display means, and scrolling the reaction path diagram displayed on said display means so as to display said undisplayed compound on said display means.

Also, in this case, said step of scrolling the reaction path diagram may further comprise a step of obtaining a number of reaction steps from the end compound with respect to said end compound corresponding to said selected guide mark, for each of the compounds constituting the reaction path diagram displayed on said display means, and extracting a compound whose number of reaction steps obtained is not more than a second predetermined number of reaction steps. In this case, it is preferred that when scrolling said reaction path diagram, said undisplayed compound be displayed on said display means while displaying said extracted compound on the display means.

Further, in this case, in the displaying method of reaction path diagram of the compound of the present invention, said step of scrolling the reaction path diagram may further comprise:

a step of reading an enzyme number of an enzyme for which the undisplayed compound is a substrate and an enzyme number of an enzyme by which the undisplayed compound is a product out of said relation information file, based on the compound number of said undisplayed compound, a step of reading a compound number of a compound being a substrate for the enzyme and a compound number of a compound being a product by the enzyme out of said enzyme information file, based on the enzyme number of each of the enzymes read in the foregoing step, and a step of adding to said reaction path information file the compound numbers of the compounds and the enzyme numbers of the enzymes read in the foregoing steps.

In the displaying method of reaction path diagram of compound of the present invention stated above, it is preferred that said guide mark be displayed near said end compound accompanied by the undisplayed, adjacent reaction, and that said guide mark be a mark indicating direction of said undisplayed, adjacent reaction. Further, said reaction path diagram may be scrolled according to a predetermined number of scrolling steps at a time.

BRIEF DESCRIPTION OF THE DRAWINGS

FIG. 3 is a drawing to show an example of the structure of a compound information file according to the present invention.

FIG. 4 is a drawing to show an example of the structure of an enzyme information file according to the present invention.

FIG. 5 is a drawing to show an example of the structure of a relation information file according to the present invention.

FIG. 8A and FIG. 8B are drawings to show specific examples of image data, respectively, and FIG. 8C is a drawing to show a specific example of canonical data corresponding to the image data.

BEST MODE FOR CARRYING OUT THE INVENTION

The preferred embodiments of the present invention will be described with reference to the accompanying drawings. First explained is an embodiment of the biochemical information processing apparatus which embodies the displaying method of reaction path diagram of compound according to the present invention.

Figure 1:
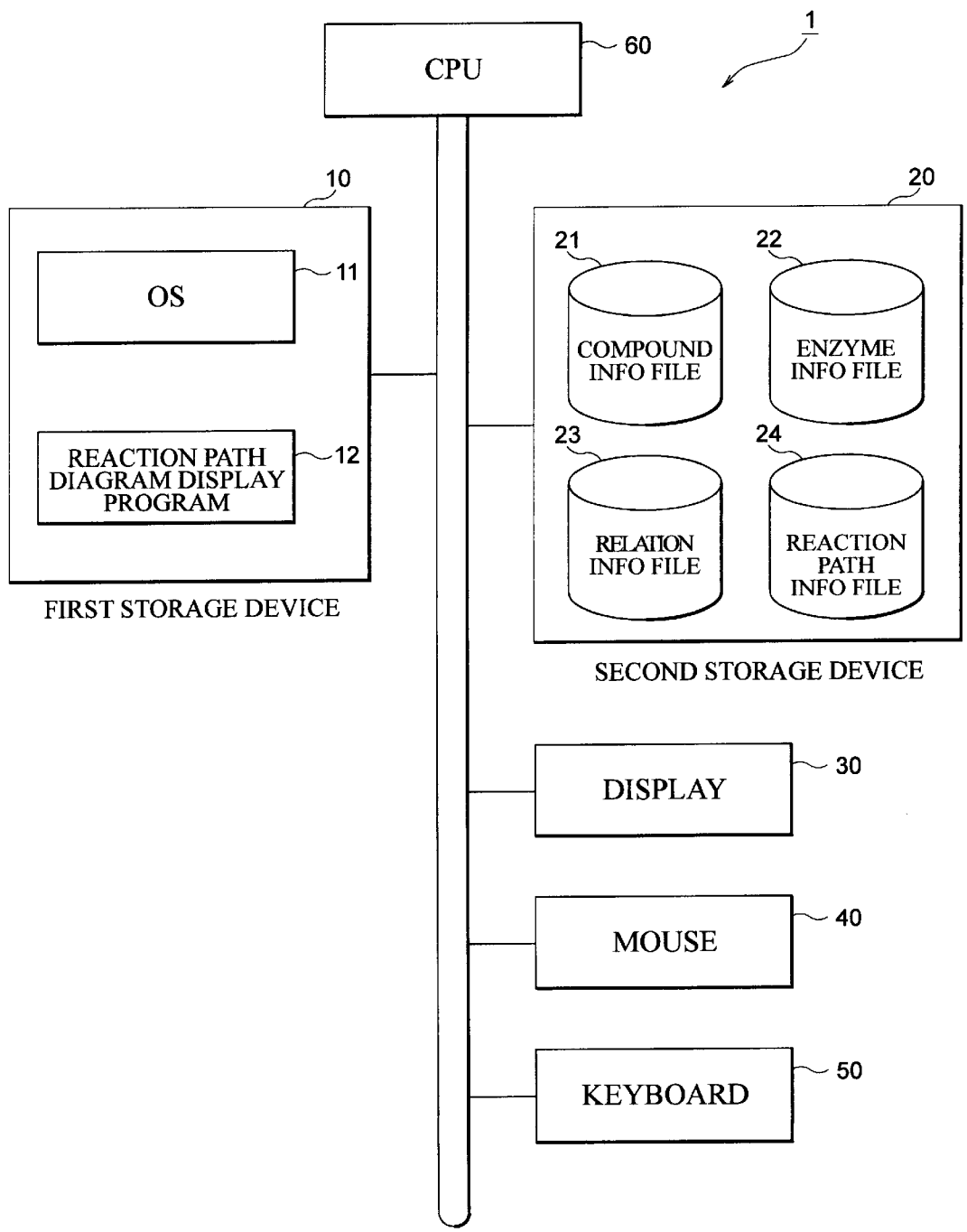
FIG. 1 is a block diagram to show an example of biochemical information processing apparatus according to the present invention.

FIG. 1 is a block diagram to show the biochemical information processing apparatus 1 for displaying a reaction path diagram of enzyme reaction such as metabolism in vivo. As shown in FIG. 1, the biochemical information processing apparatus 1 has a first storage device 10 storing an operating system (OS) 11 and a reaction path diagram displaying program 12, a second storage device 20 storing the files described below, a display 30 being display means, a mouse 40 for accepting a selection of guide mark, a keyboard 50 for accepting an input of alpha-numeric string, and a CPU 60 for controlling execution of the reaction path diagram displaying program 12.

In the displaying method of reaction path of compound according to the present invention, the reaction path diagram displaying program 12 stored in the first storage device 10 is initiated to display a reaction path diagram on the display 30, and to scroll the reaction path diagram along the reaction path. The reaction path diagram is prepared based on the files stored in the second storage device 20. The second storage device 20 stores a compound information file 21, an enzyme information file 22, a relation information file 23, and a reaction path information file 24. Reference is made to these files 21–24 at execution of the reaction path diagram displaying program 12, and a reaction path diagram is prepared to include a couple of reaction steps before and after a predetermined compound at the center. Here, the number of reaction steps means the number of unit reaction schemes (formulas). For example, a reaction path diagram of one reaction step after the center (reference) of the predetermined compound is a single reaction scheme in that the predetermined compound is a starting material. Further, a reaction path diagram of one reaction step before the center (reference) of the predetermined compound is a single reaction scheme in that the predetermined compound is a product.

Among the files stored in the second storage device 20, the compound information file 21 stores a list to show the relationship between compound numbers and canonical data (also referred to as canonical data) corresponding to the compounds, and additional information (for example, the reference data of FIG. 3) about the compounds. Further, the enzyme information file 22 stores a list to show the relationship among enzyme numbers as keys, compound numbers of compounds being substrates (starting materials) for the enzymes, and compound numbers of compounds being products by the enzymes, and additional information (for example, the reference data of FIG. 4) about the enzymes. Furthermore, the relation information file 23 stores a list to show the relationship among compound numbers as keys, enzyme numbers of enzymes for which the compounds are substrates, and enzyme numbers of enzymes by which the compounds are products. Moreover, the reaction path information file 24 stores reaction path information prepared by execution of the reaction path diagram displaying program 12.

Figure 2:
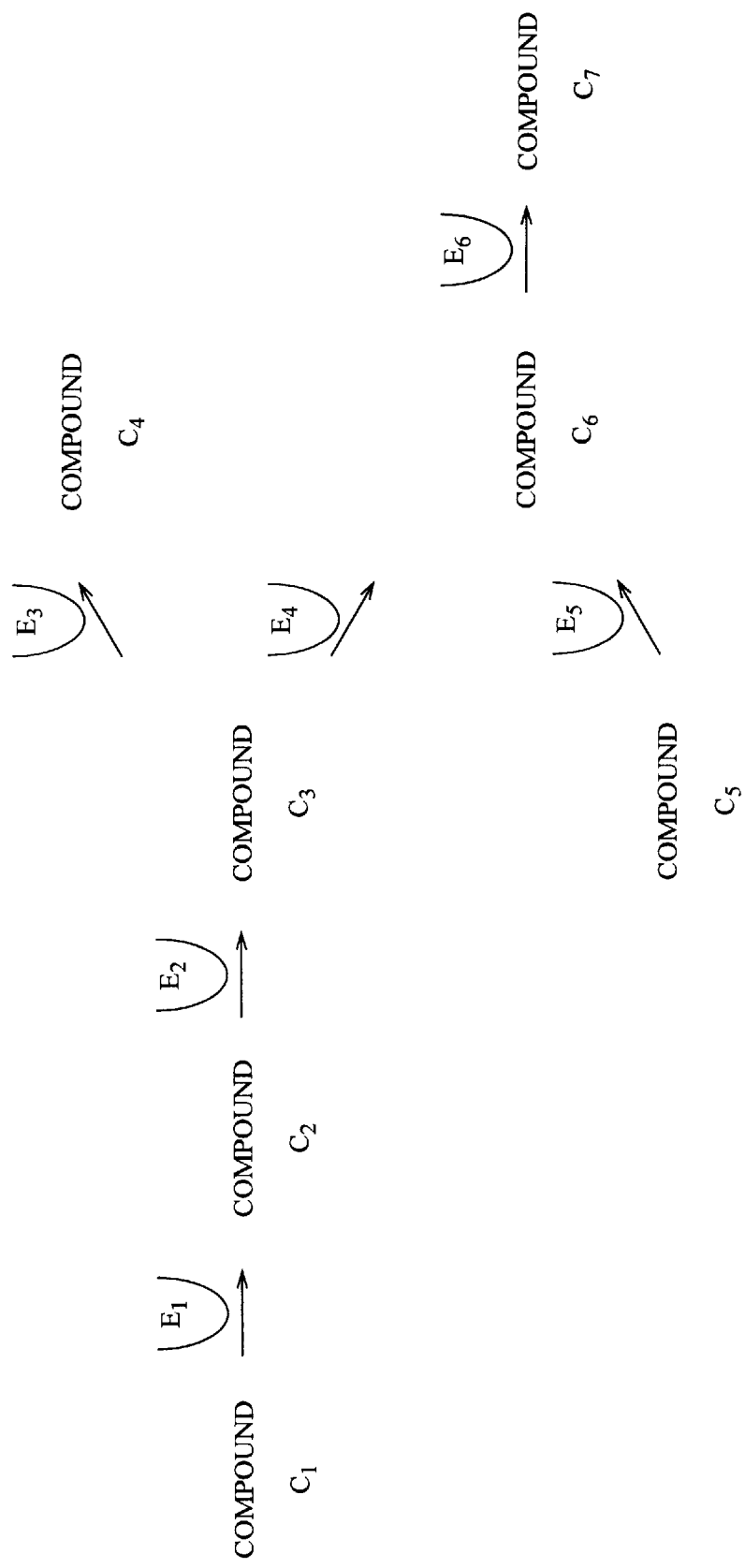
FIG. 2 is an example of a reaction path diagram to show a path in which a compound of compound number $C_1$ changes up to a compound of compound number $C_7$.

Next explained is the detailed structure of the compound information file 21, enzyme information file 22, and relation information file 23 with reference to FIG. 2 to FIG. 5. FIG. 2 is an example of a reaction path diagram to show a path through which a compound of compound number $C_1$ changes in order to compounds of compound numbers $C_2$, $C_3$, . . . with plural enzymes of enzyme numbers $E_1$ to $E_6$ as catalysts, finally changing into a compound of compound number $C_7$.

The compound numbers $C_1$–$C_7$ described in this example of reaction path diagram are recorded in the compound information file 21 shown in FIG. 3. The compound information file 21 includes a record of canonical data corresponding to each compound of compound number $C_1$–$C_7$, and the reference data (name of compound, physical properties, literature, etc.) about each compound of compound number $C_1$–$C_7$ in the form of a list corresponding to the compound numbers $C_1$–$C_7$. When access is made to the compound information file 21, using the compound number $C_1$–$C_7$ as a key, the canonical data and reference data can be read out as to each compound of compound number $C_1$–$C_7$. Here, the canonical data is a plurality of symbolic data for uniquely specifying the chemical structure of each compound, the details of which will be described hereinafter.

The enzyme numbers $E_1$–$E_6$ described in the example of reaction path diagram of FIG. 2 are recorded in the enzyme information file 22 shown in FIG. 4. The enzyme information file 22 includes a record of the compound numbers $C_1$–$C_6$ (excluding $C_4$) of the compounds being substrates for the respective enzymes of enzyme numbers $E_1$–$E_6$, the compound numbers $C_2$–$C_7$ (excluding $C_5$) of the compounds being products by the respective enzymes of enzyme numbers $E_1$–$E_6$, and the reference data (name, literature, physical properties, inhibitor, inducer, activator, etc.) about each enzyme of enzyme number $E_1$–$E_6$ in the form of a list corresponding to the enzyme numbers $E_1$–$E_6$.

Therefore, when access is made to the enzyme information file 22, using the enzyme number $E_1$–$E_6$ as a key, the compound numbers $C_1$–$C_7$ of compounds being a substrate and a product for each enzyme of enzyme number $E_1$–$E_6$, and the reference data can be read out. It is also possible to similarly handle reactions by enzymes not classified as enzyme or by those not identified as enzyme yet, nonenzymatic reactions involving light, heat, acid, base, metal ion, or the like, and multi-step reactions by a plurality of enzymes, by describing each of them with an enzyme number.

Further, the relation among the compound numbers $C_1$–$C_7$ and enzyme numbers $E_1$–$E_6$ described in the reaction path diagram of FIG. 2 is recorded in the relation information file 23 shown in FIG. 5. Describing in more detail, the enzyme numbers $E_1$–$E_6$ of enzymes for which the respective compounds of compound numbers $C_1$–$C_6$ (excluding $C_4$) are substrates, the enzyme numbers $E_1$–$E_6$ (Excluding $E_4$) of enzymes by which the respective compounds of compound numbers $C_2$–$C_7$ (excluding $C_5$) are products, and the enzyme number $E_4$ of the enzyme inhibited by the compound of compound number $C_6$ are recorded in the form of a list corresponding to the compound numbers $C_1$–$C_7$. Therefore, when access is made to the relation information file 23, using the compound number $C_1$–$C_7$ as a key, it is possible to read the enzyme numbers $E_1$–$E_6$ of enzymes for each compound of compound number $C_1$–$C_7$ as a substrate or as a product, and the enzyme number $E_4$ of the enzyme inhibited by the compound of compound number $C_6$.

Next, the data contents of the enzyme information file 22 will be explained specifically. First, from the reaction path diagram of FIG. 2, a compound number of a compound being a substrate for the enzyme of the enzyme number $E_1$ is $C_1$. A compound number of a compound being a product by the enzyme of the enzyme number $E_1$ is $C_2$. Therefore, $C_1$ is recorded in the column of (substrate) compound number corresponding to the enzyme number $E_1$ in the enzyme information file 22 of FIG. 4. In addition, $C_2$ is recorded in the column of (product) compound number corresponding to the enzyme number $E_1$.

Similarly, from the reaction path diagram of FIG. 2, a compound number of a compound being a substrate for the enzyme of the enzyme number $E_2$ is $C_2$. Further, a compound number of a compound being a product by the enzyme of the enzyme number $E_2$ is $C_3$. Therefore, $C_2$ is recorded in the column of (substrate) compound number corresponding to the enzyme number $E_2$ in the enzyme information file 22 of FIG. 4. Also, $C_3$ is recorded in the column of (product) compound number corresponding to the enzyme number $E_2$.

Such relation also holds for the enzyme numbers $E_3$–$E_6$ similarly, so that the compound numbers $C_3$–$C_7$ along the reaction path diagram of FIG. 2 are recorded in each of the columns of (substrate) compound number and (product) compound number corresponding to the enzyme numbers $E_3$–$E_6$.

Next, the data contents of the relation information file 23 will be described specifically. First, from the reaction path diagram of FIG. 2, the enzyme number of the enzyme for which the compound of the compound number $C_1$ is a substrate is $E_1$. Therefore, $E_1$ is recorded in the column of (substrate) enzyme number corresponding to the compound number $C_1$ in the relation information file 23 of FIG. 5.

Similarly, from the reaction path diagram of FIG. 2, the enzyme number of the enzyme for which the compound of the compound number $C_2$ is a substrate is $E_2$. Also, the enzyme number of the enzyme by which the compound of the compound number $C_2$ is a product is $E_1$. Therefore, $E_2$ is recorded in the column of (substrate) enzyme number corresponding to the compound number $C_2$ in the relation information file 23 of FIG. 5. Also, $E_1$ is recorded in the column of (product) enzyme number corresponding to the compound number $C_2$.

Such relation also holds for the compound numbers $C_3$–$C_7$ similarly, so that the enzyme numbers $E_2$–$E_6$ along the reaction path diagram of FIG. 2 are recorded in each of the columns of (substrate) enzyme number and (product) enzyme number corresponding to the compound numbers $C_3$–$C_7$. Further, the compound of the compound number $C_6$ is a substrate for the enzyme number $E_6$ and a product by the enzyme number $E_5$, while being an inhibitor for the enzyme number $E_4$, and thus, $E_4$ is recorded in the column of (inhibitor) enzyme number.

Here, the chemical structure of compounds does not always have to be specified by the above canonical data, but may be specified by their molecular structure diagrams. Further, a molecular structure diagram may be image data, or bond table data or table composed of two-dimensional coordinate data on the display 30, of each of atoms constituting the molecular structure diagram. The bond table data should preferably include the number of atom, the number of bonds, an element name of each atom, and a type of each bond (single bond, double bond, etc.), for example. Using the bond table data, structures of all compounds can be expressed as numerical data.

Figure 6A:
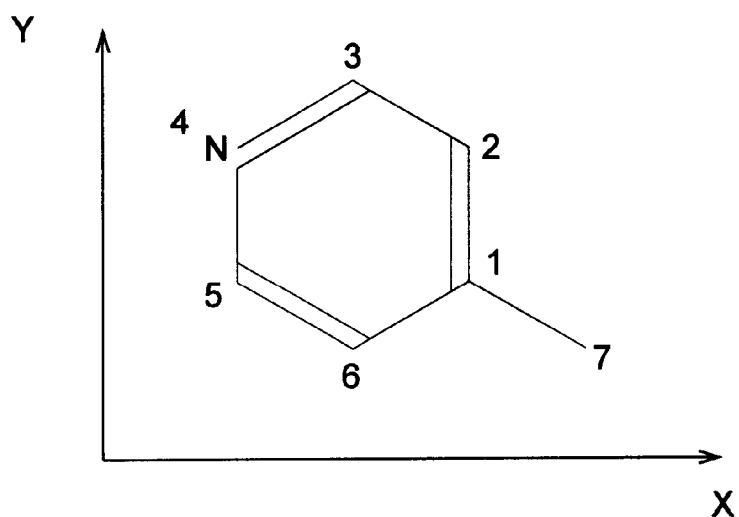
FIG. 6A is a drawing to show a specific example of image data, FIG. 6B a specific example of bond table data, and FIG. 6C a specific example of canonical data, respectively.

FIG. 6A to FIG. 6C show a specific example of image data 80a, bond table data 81a, and canonical data 82a. FIG. 6A is the image data 80a to show the molecular structure of compound "4-methylpyridine". This image data 80a can be converted to the bond table data 81a shown in FIG. 6B. The bond table data 81a is a table in which the number of atoms, the number of bonds, coordinates of each atom, an element name of each element, and so on are recorded. Using this bond table data 81a, structures of all compounds can be expressed as numerical data.

Further, the bond table data 81a can be converted to the canonical data 82a shown in FIG. 6C. The canonical data 82a is a symbolic string including an array of numerals, marks, and so on. As shown in FIG. 6C, the canonical data 82a of compound "4-methylpyridine" is "1%1%1–2%3%5%N/6%7/". In this way, the canonical data 82a can express the structure of a compound in the form of a very short symbolic string. Because of it, if this canonical data 82a is applied, for example, to a compound search system, the search speed can be increased and the storage resource can be effectively utilized.

Figure 7A:
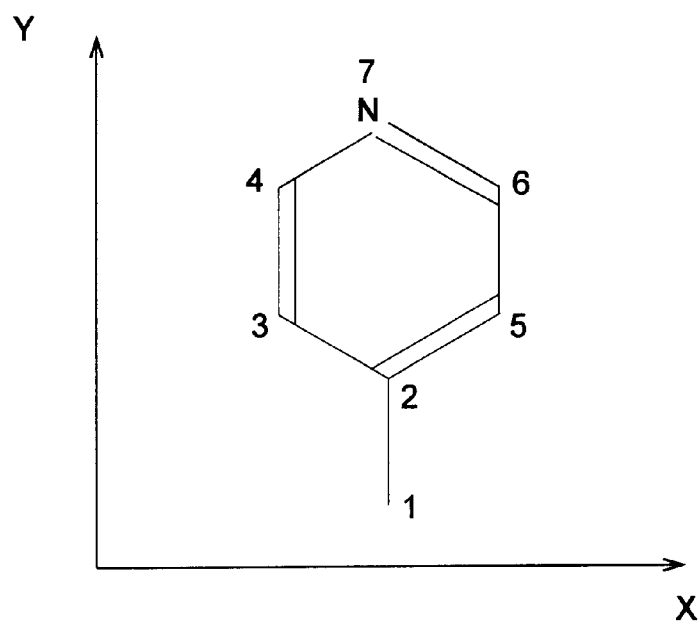
FIG. 7A is a drawing to show a specific example of image data, FIG. 7B a specific example of bond table data, and FIG. 7C a specific example of canonical data, respectively.
Figure 9:
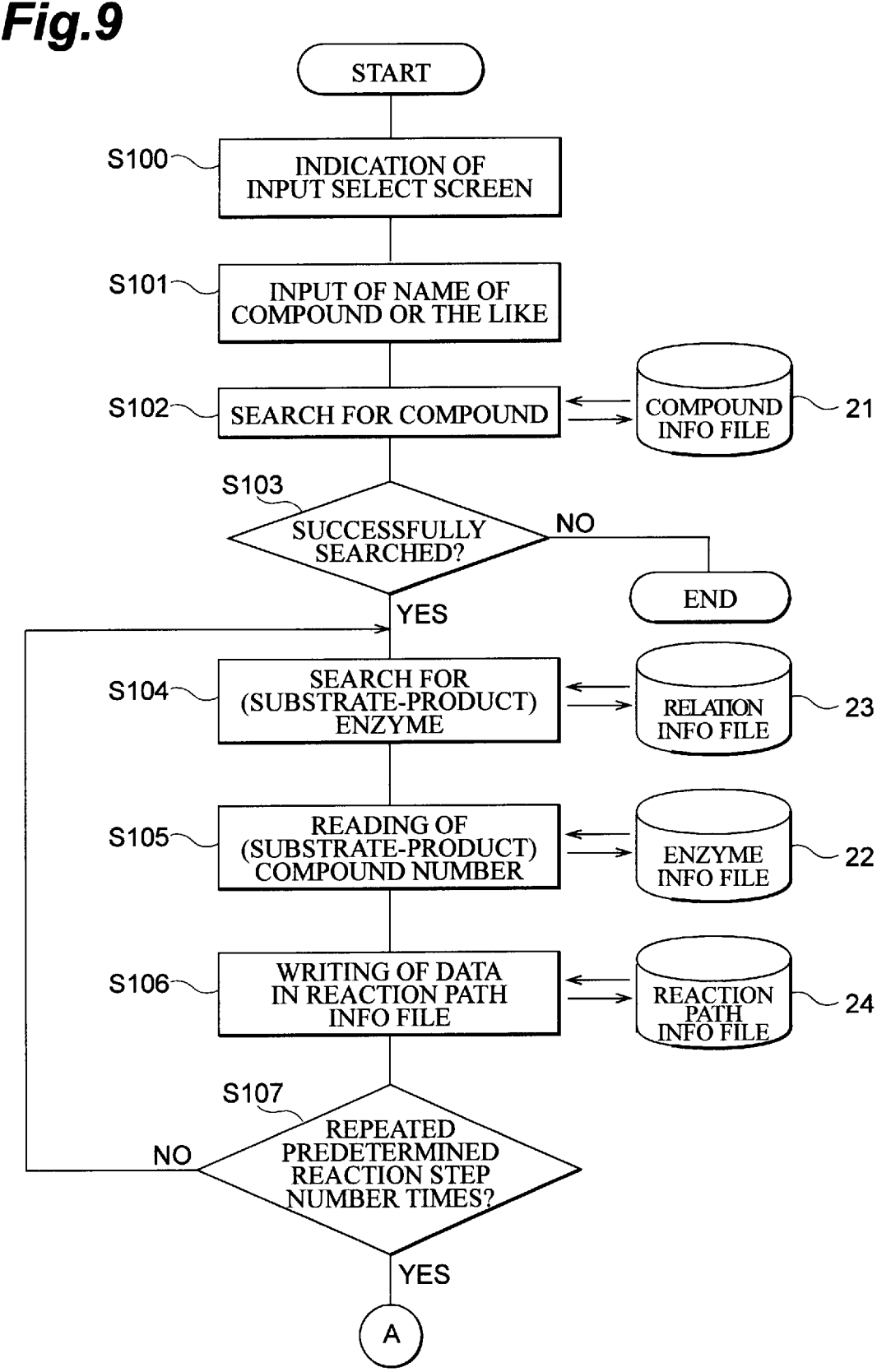
FIG. 9 is a flowchart to show the flow of process of a program for displaying the reaction path diagram according to the present invention.

There are, however, some cases wherein a compound cannot be uniquely specified by the bond table data described above, and it is thus not a good idea to apply the bond table data to the compound search system. Namely, as shown in FIG. 7A to FIG. 7C, the image data 80b is the data expressing the same compound as the image data 80a, but the bond table data 81b is utterly different from the bond table data 81a. It is seen from this result that a compound cannot be always uniquely specified from the bond table data. In contrast with it, the canonical data 82b obtained by converting the bond table data 81b is the same as the canonical data 82a, and can uniquely specify the compound.

Particularly, as shown in FIG. 8A to FIG. 8C, two image data 80c, 80d are completely different in appearance from each other, though the both are image data indicating an identical compound. The canonical data 82c resulting from conversion of such image data 80c, 80d is the same, thus proving that the canonical data can uniquely specify a compound.

As described, the canonical data is more excellent than the bond table data in that it can uniquely specify a compound, and therefore, the canonical data is mainly used in the present embodiment.

On the other hand, since the bond table data includes two-dimensional coordinate data, it is easy to display the molecular structure diagram of compound on the display 30 by use of the bond table data. Further, the two-dimensional coordinate data (X-coordinate and Y-coordinate) can be obtained by calculation from other data in the bond table data (though it is of course necessary to preliminarily designate the lengths of bonds, angles between bonds, the position of the center when displayed on the display, and so on). Therefore, when each compound is expressed by a molecular structure diagram in the reaction path diagram, it is preferred that the bond data file be also stored in the compound information file 21 of the second storage device 20.

The above-stated canonical data, image data, and bond table data can be converted to each other by existing conversion algorithms. For example, conversion between the image data and the bond table data can be effected by use of a graphic library ready for the OS used. Further, algorithms applicable for the aforementioned conversion between the bond table data and the canonical data include the known Morgan algorithm (H. L. Morgan, J. Chem. Doc., 5(2), 107 (1965)), the conversion algorithm by the present inventors as described in "Abstracts, The 13th symposium of information science, p 25,", and the conversion algorithm by the present inventors as described in the official gazette of International Publication Number WO96/29659. However, the above-stated first conventional conversion algorithm by the present inventors was able to obtain the canonical data more quickly than the Morgan algorithm without intervention of the process for classifying atoms under equivalent atoms, but, because the attribute of each atom used therein was the number of atoms located at a specific minimum distance from the pertinent atom, it lacked preciseness of determination of equivalent atom and thus the reliability of canonical data obtained was not sufficient yet. Accordingly, the present embodiment particularly preferably employs the canonical data preparation method detailed in the gazette of International Publication Number WO96/29659. Here, the gazette is incorporated herein by reference.

Described next is a method for displaying a reaction path diagram of compound by use of the biochemical information processing apparatus 1. First, the reaction path diagram display program 12 is started under control of the OS 11.

In the reaction path diagram display program 12, as shown in the flowcharts of FIG. 9 to FIG. 13, an input screen for input of alpha-numeric string is displayed on the display 30 (S100). When the operator next gives an input of alpha-numeric string such as a name of a compound or a chemical formula for specifying a predetermined center compound (a compound to be displayed at the center of a reaction path) through the keyboard 50, this input is accepted (S101). Then a search for the center compound specified by this alpha-numeric string is carried out through the compound information file 21 (S102).

If this search process results in finding no canonical data coincident with that of the center compound in the compound information file 21 (S103), the process will be terminated. In contrast with it, when there exists the canonical data coincident with that of the center compound in the compound information file 21, a compound number corresponding to this canonical data is read out of the compound information file 21.

The processes from S100 to S102 may be done by steps of displaying a screen for drawing a molecular structure diagram on the display 30, allowing the operator to give an input of molecular structure diagram indicating the structure of the predetermined center compound through the mouse 40 or the like, and accepting the graphic data. In this case, the molecular structure diagram drawn is converted to bond table data and further to canonical data according to the known conversion algorithms, and the search for the center compound is carried out through the compound information file 21, using the canonical data obtained by the conversion.

Figure 10:
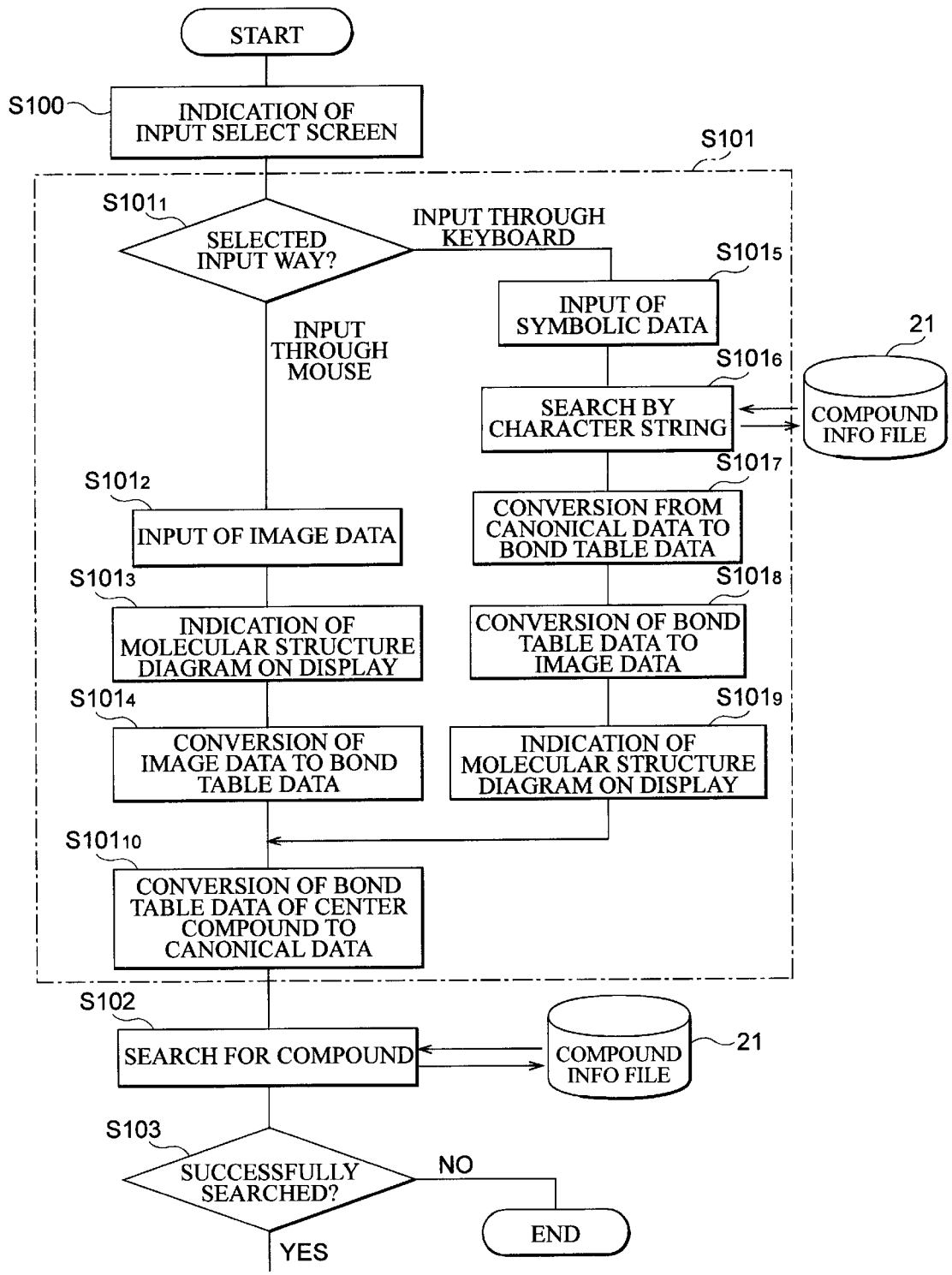
FIG. 10 is a flowchart to show the detailed process of S101 shown in FIG. 9.

The above-stated input process of compound name or the like (S101) is detailed in FIG. 10. As shown in the flowchart of FIG. 10, the reaction path diagram display program 12 is arranged first to display a select screen of input method on the display 30 (S100). When the operator selects the input through the mouse 40 according to this screen indication (S101$_1$), the screen for drawing of molecular structure diagram is displayed on the display 30. When the operator gives an input of molecular structural diagram indicating the structure of the predetermined compound through the mouse 40, this diagram is accepted as image data to be stored in an image memory (S101$_2$). This image data is also displayed on the display 30 (S101$_3$). Then this image data is converted to the bond table data according to the aforementioned conversion algorithm (S101$_4$).

When the operator selects the input through the keyboard 50 according to the screen indication of S100 (S101$_1$), a screen for input of symbol string is displayed on the display 30. When the operator gives an input of symbol string such as a name of a compound or a chemical formula specifying the predetermined compound through the keyboard 50, this input is accepted (S101$_5$). Then the search for the compound specified by this symbol string (S101$_6$) is carried out through the compound information file 21, and the bond table data is made from the canonical data of the pertinent compound (S101$_7$). Then this bond table data is converted to image data, based on the aforementioned two-dimensional coordinate data (S101$_8$) and this image data is displayed on the display 30 (S101$_9$). On the other hand, when symbol data a name of an enzyme or the like is given through the keyboard 50, a search based on the character string (S101$_6$) is carried out through the enzyme information file 22 to read a number of the pertinent enzyme out thereof, and it can be used in the processes as described above.

After completion of the process of S103 described previously, based on the compound number read in S102, an enzyme number of an enzyme for which the compound is a substrate and an enzyme number of an enzyme by which the compound is a product are read out of the relation information file 23 (S104). Further, based on each of the enzyme numbers read in S104, a compound number of a compound as a substrate for this enzyme and a compound number of a compound as a product by this enzyme are read out of the enzyme information file 22 (S105). Then the compound number read in S102, the enzyme numbers read in S104, and the compound numbers read in S105 are successively written into the reaction path information file 24 (S106).

The processes up to this point result in extracting reactions one reaction step before and after the center compound. For example, in the case of the enzyme information file of FIG. 4 and the relation information file of FIG. 5, when the center compound is $C_3$, the compounds and enzymes involved in the reactions $C_2 \rightarrow C_3$, $C_3 \rightarrow C_4$, and $C_3 \rightarrow C_6$ are written in the reaction path information file 24. Subsequently, the processes from S104 to S106 are repeated a predetermined reaction step number times (times according to a first predetermined number of reaction steps) (S107), and compound numbers of all compounds and enzyme numbers of all enzymes constituting the reaction path diagram to be displayed on the display 30 are written in the reaction path information file 24. The first predetermined number of reaction steps used in S107 is the number of reaction steps to be displayed on the display 30, which is preliminarily set by the operator. This number of reaction steps is preliminarily set, for example, so that one upstream reaction step and two downstream reaction steps are displayed for the center of the center compound.

Figure 14:
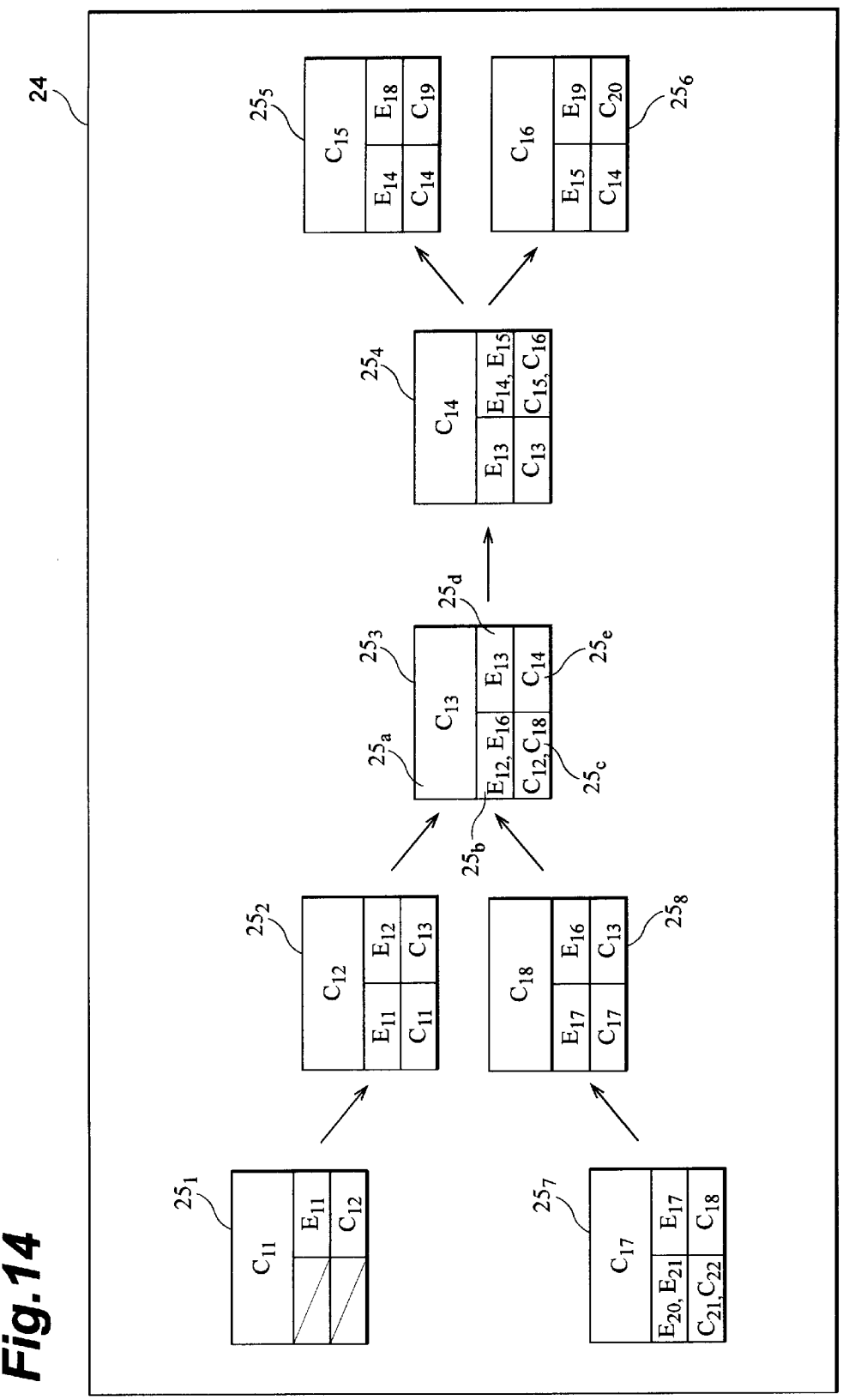
FIG. 14 is a drawing to show an example of internal structure of the reaction path information file (before scrolling) according to the present invention.

The reaction path information file 24 is a file storing a plurality of connection tables $25_1$, to $25_8$, as shown in FIG. 14. Each connection table $25_1$–$25_8$ is provided with a member area 25*a* for storing a compound number, a member area 25*b* for storing an enzyme number of an enzyme by which the compound indicated by this compound number is a product, and a member area 25*c* for storing a compound number of a compound as a substrate for this enzyme. Further, each connection table $25_1$–$25_8$ is provided with a member area 25*d* for storing an enzyme number of an enzyme for which the compound indicated by the compound number stored in the member area 25*a* is a substrate, and a member area 25*e* for storing a compound number of a compound as a product by this enzyme.

Accordingly, the process of S106 stores the compound number read in S102 in the member area 25*a*. The process of S106 also stores the enzyme numbers read in S104 in the member areas 25*b* (on the substrate side), 25*d* (on the product side). Further, the process of S106 stores the compound numbers read in S105 in the member areas 25*c* (on the substrate side), 25*e* (on the product side). Since the process of S106 is repetitively carried out as described above, in the case of the example shown in FIG. 14, reaction path information within the range of two reaction steps before and after the center compound being the compound of the compound number $C_{13}$ is stored in the reaction path information file 24.

Figure 11:
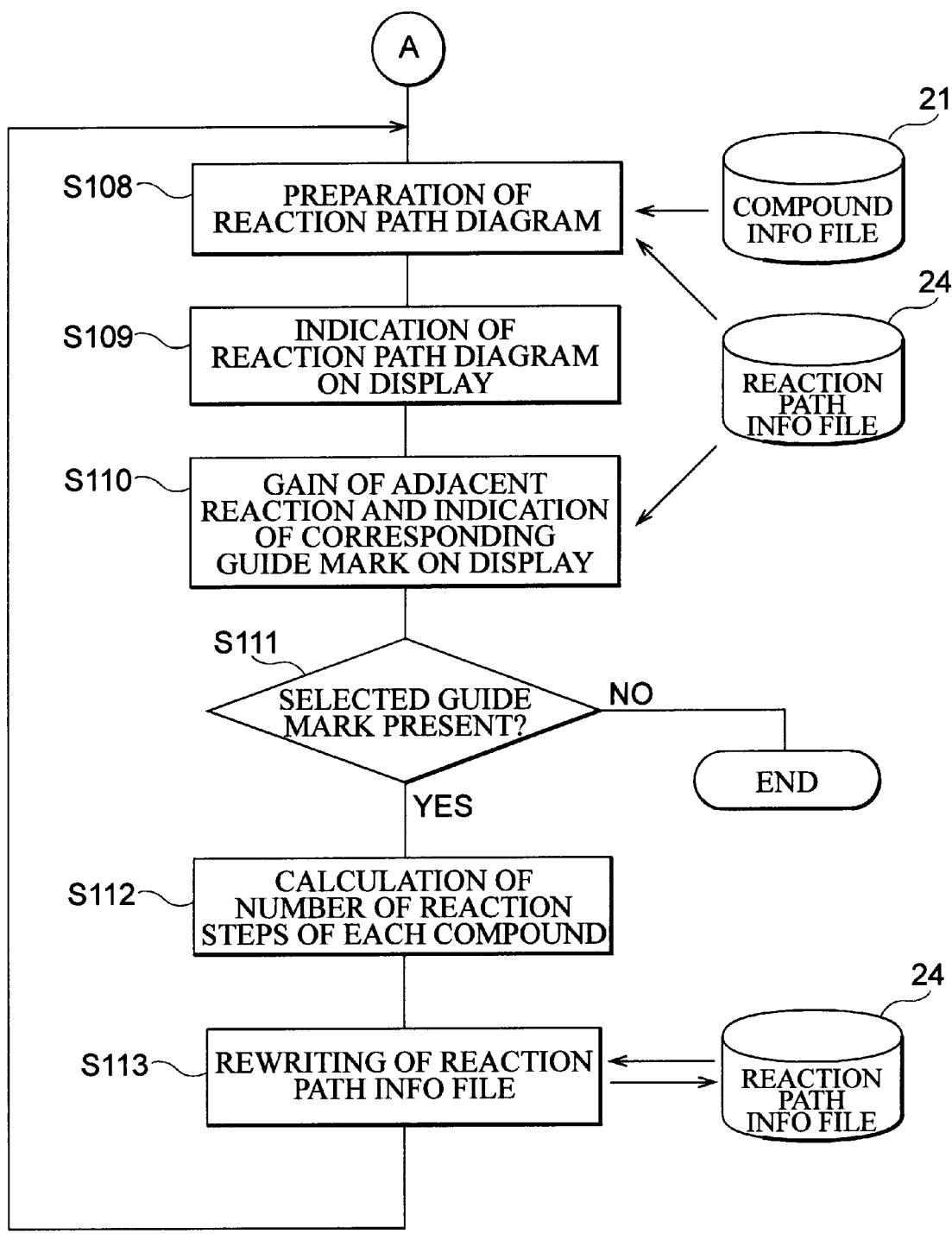
FIG. 11 is a flowchart to show the flow of process of the program for displaying the reaction path diagram according to the present invention.
Figure 15:
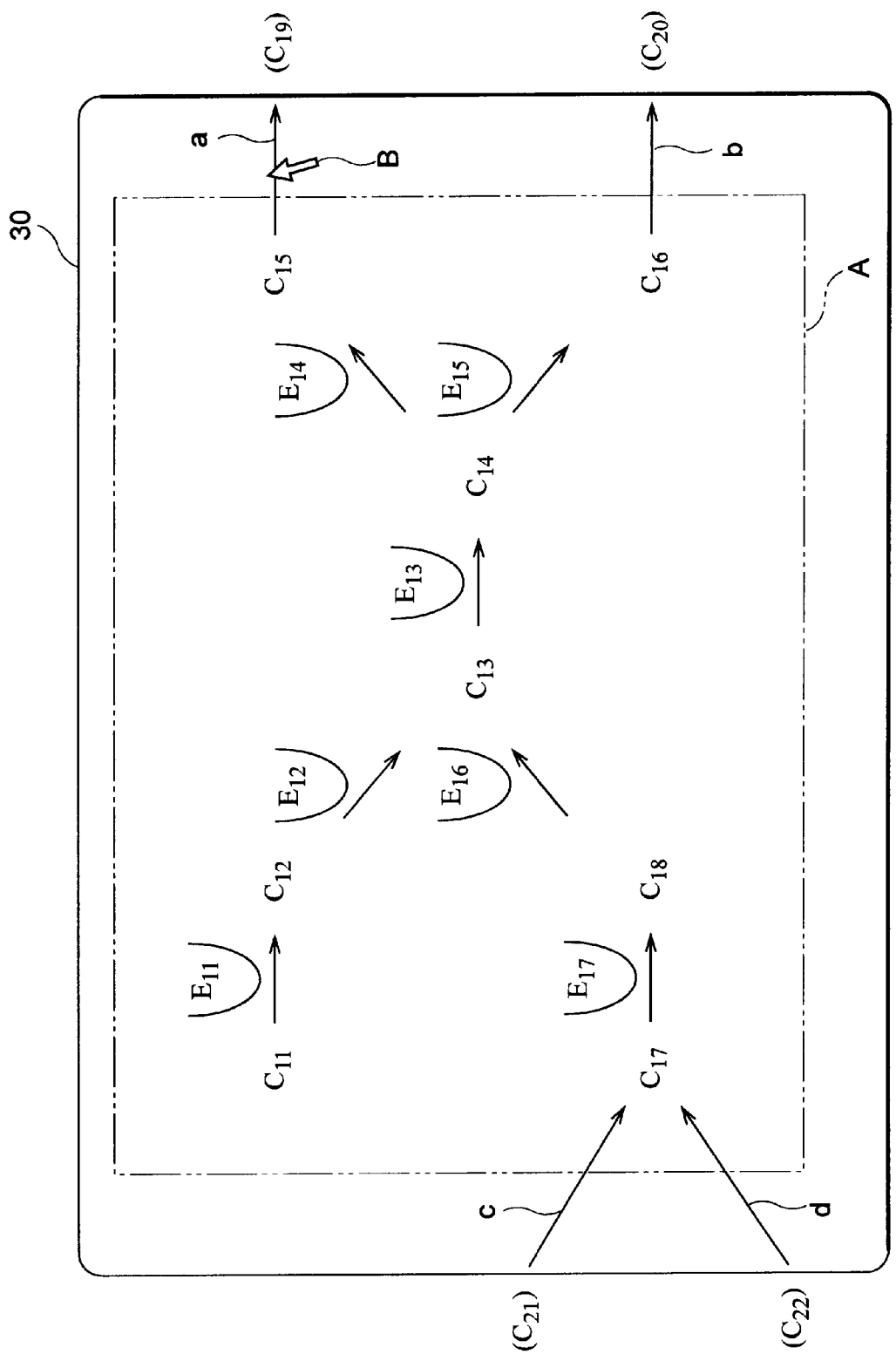
FIG. 15 is a drawing to show a display example of the reaction path diagram (before scrolling) according to the present invention, on the display.

Then, as shown in the flowchart of FIG. 11, the reaction path information stored in the reaction path information file 24 is read to prepare a reaction path diagram based on this reaction path information (S108). Here, the molecular structure of each compound forming the reaction path diagram is specified based on the canonical data of compound information file 21 or the bond table data. Then this reaction path diagram A is displayed on the display 30, as shown in FIG. 15 (S109). The indication of the compounds $C_1$–$C_{18}$ on the reaction path diagram A may be given by their compound names or their abbreviated forms, but they are preferably indicated by the molecular structure diagram in view of easiness of operator's recognition. The molecular structure diagram displayed can also be calculated from the canonical data of compound as described previously, but a preferred way is that the column of bond table data is provided in the compound information file 21, the bond table data corresponding to the compounds is preliminarily stored in the compound information file 21, and the bond table data is utilized from the file. Namely, the conversion from a compound number to a molecular structure diagram may be carried out, for example, in the order of compound number→bond table data (with access to the compound information file)→molecular structure diagram (using two-dimensional coordinates) The image data of reaction path diagram is displayed on the display 30, preferably, in such a layout that an arrow combines a molecular structure diagram of a compound of a (substrate) compound number with a molecular structure diagram of a compound of a (product) compound number, obtained above, and that the reference data of an enzyme (especially, a name thereof) is placed near the arrow.

Figure 12:
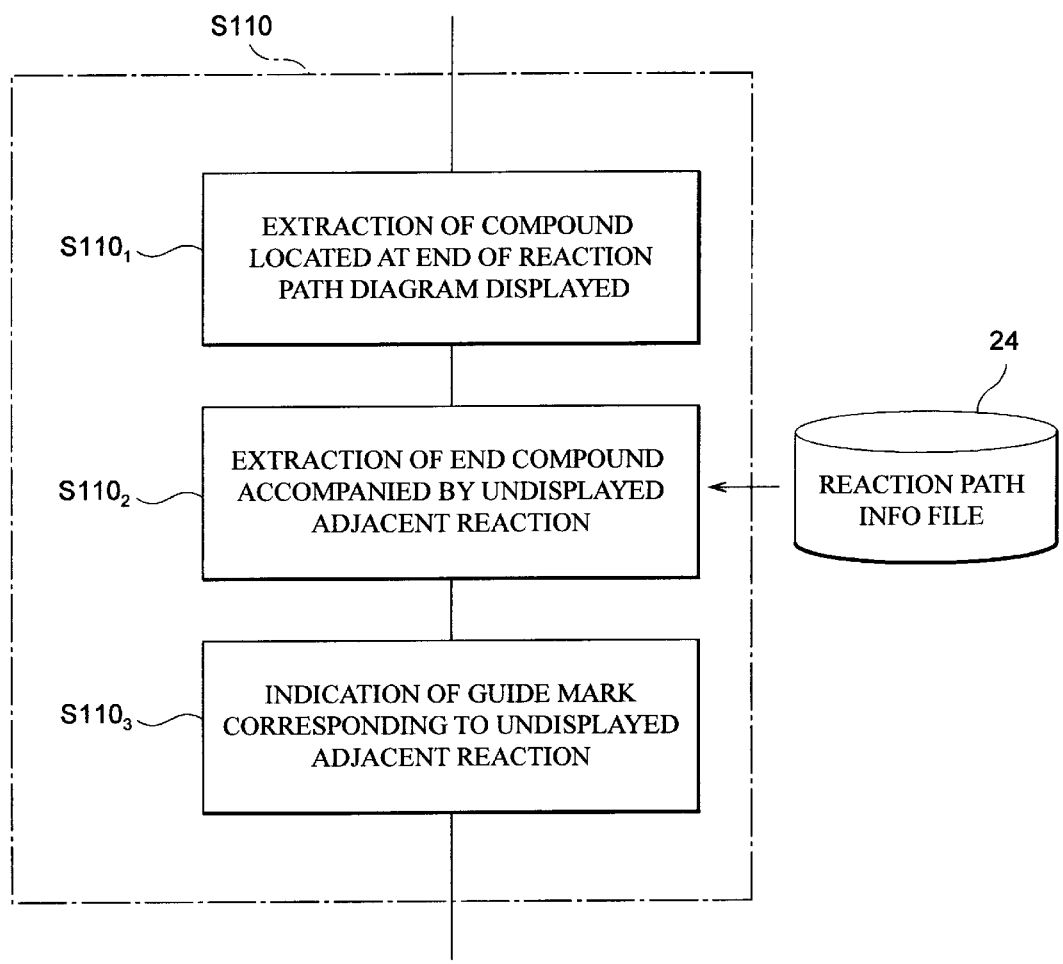
FIG. 12 is a flowchart to show the detailed process of S110 shown in FIG. 11.

Subsequently, as shown in FIG. 12, reference is made to the reaction path information file 24 to extract every end compound (compound numbers $C_{11}$, $C_{15}$, $C_{16}$, $C_{17}$) that is located at the end of this reaction path diagram A, out of the compounds constituting the reaction path diagram A displayed on the display 30 (S110$_1$). Then an end compound accompanied by an undisplayed, adjacent reaction that is an adjacent reaction thereto and is not displayed on the display 30, i.e. $C_{15}$, $C_{16}$, $C_{17}$, is extracted out of the extracted end compounds $C_{11}$, $C_{15}$, $C_{16}$, $C_{17}$ (S110$_2$). Here, presence or absence of an undisplayed, adjacent reaction of end compound is obtained from the reaction path information file 24 shown in FIG. 14.

Specifically, the connection tables 25$_1$, 25$_5$, 25$_6$, 25$_7$ storing their respective compound numbers $C_{11}$, $C_{15}$, $C_{16}$, $C_{17}$ in the member area 25*a* are first extracted as tables about the end compounds out of the connection tables 25$_1$–25$_8$ of the reaction path information file 24. If the connection table of these end compounds stores data in the all member areas 25*b*–25*e* (particularly, 25*c* and 25*e*), it will be determined to be a connection table 25$_5$, 25$_6$, 25$_7$ representing an end compound accompanied by an undisplayed, adjacent reaction. Namely, the connection table 25$_5$, 25$_6$, 25$_7$ in which a compound number of a compound not displayed on the display 30 is written in the member area 25*c* or 25*e* is determined to be a connection table of an end compound accompanied by an undisplayed, adjacent reaction.

By these processes, the compounds of the compound numbers $C_{15}$, $C_{16}$, $C_{17}$ are determined to be end compounds each accompanied by an undisplayed, adjacent reaction, and arrow a to arrow d as guide marks are displayed near these end compounds $C_{15}$, $C_{16}$, $C_{17}$ (S110$_3$). More specifically, as shown in FIG. 15, the arrow a is displayed near the compound of the compound number $C_{15}$, the arrow b near the compound of the compound number $C_{16}$, and the arrows c, d are displayed near the compound of the compound number $C_{17}$. An adjacent reaction is a reaction in which the compound is a product or a reaction in which the compound is a substrate.

Then the operator moves the mouse 40 while observing the reaction path diagram A displayed in this way on the display 30, and clicks either one of the arrow a to the arrow d with the cursor mark B thereon to select a compound corresponding to either one of the arrow a to arrow d (S111). In FIG. 15, the cursor mark B is placed on the arrow a, so that the compound of the compound number $C_{15}$ corresponding to the arrow a is selected.

Figure 16:
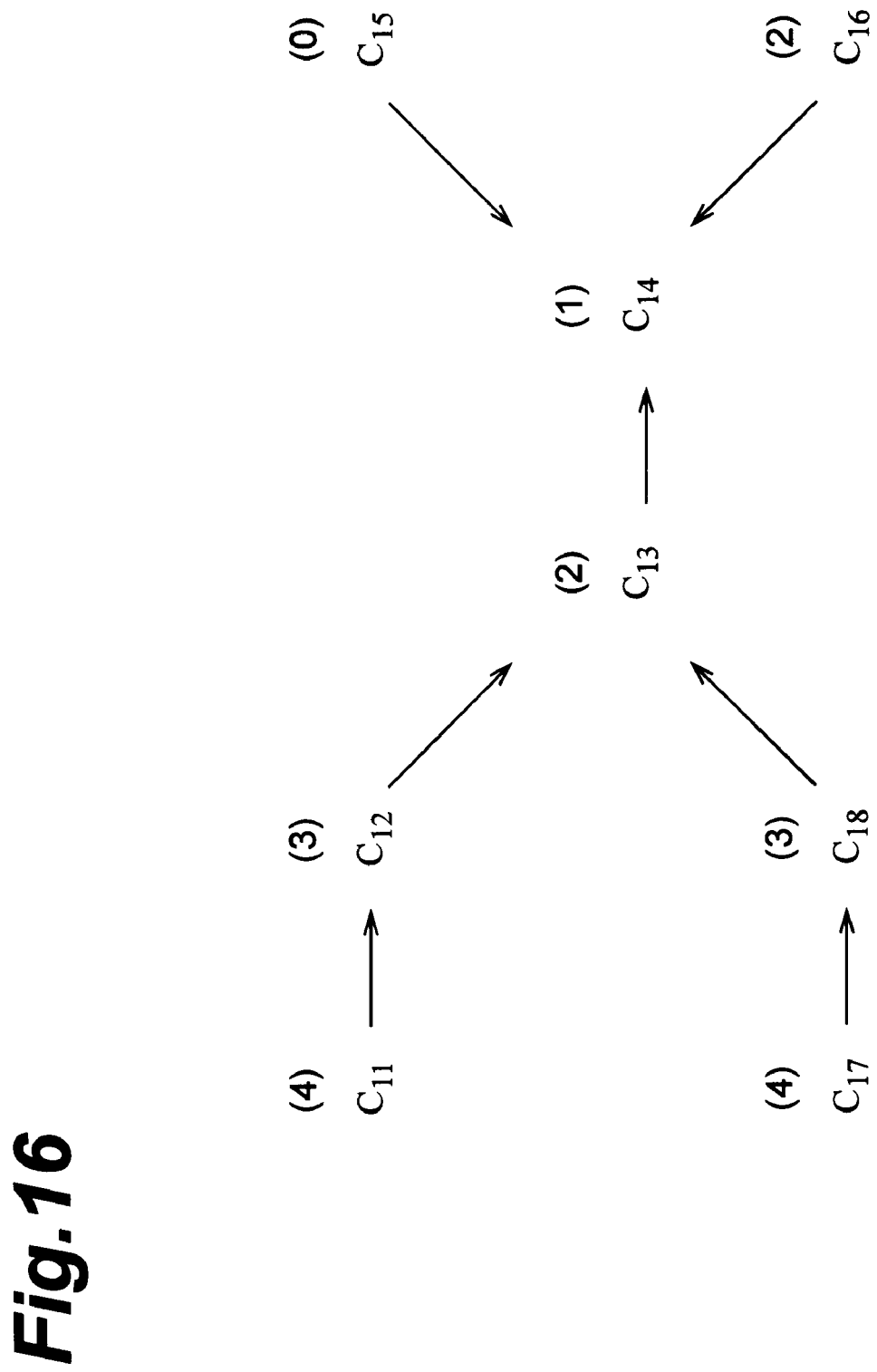
FIG. 16 is a drawing to show a calculation result of the number of reaction steps, for each of the compounds constituting the reaction path diagram shown in FIG. 15.

When the desired compound is selected, the number of reaction steps from the end compound with respect to the reference of the end compound corresponding to the selected guide mark is calculated for each of the compounds constituting the reaction path diagram A displayed on the display 30 (S112). More specifically, as shown in FIG. 16, distances (numbers of reaction steps) are calculated with respect to the compound of the compound number $C_{15}$ selected in S111. In this example, the calculation result is as follows; the distance of the compound of the compound number $C_{14}$ is 1; the distance of the compounds of the compound numbers $C_{13}$, $C_{16}$ is 2; the distance of the compounds of the compound numbers $C_{12}$, $C_{16}$ is 3; the distance of the compounds of the compound numbers $C_{11}$, $C_{14}$ is 4.

Figure 17:
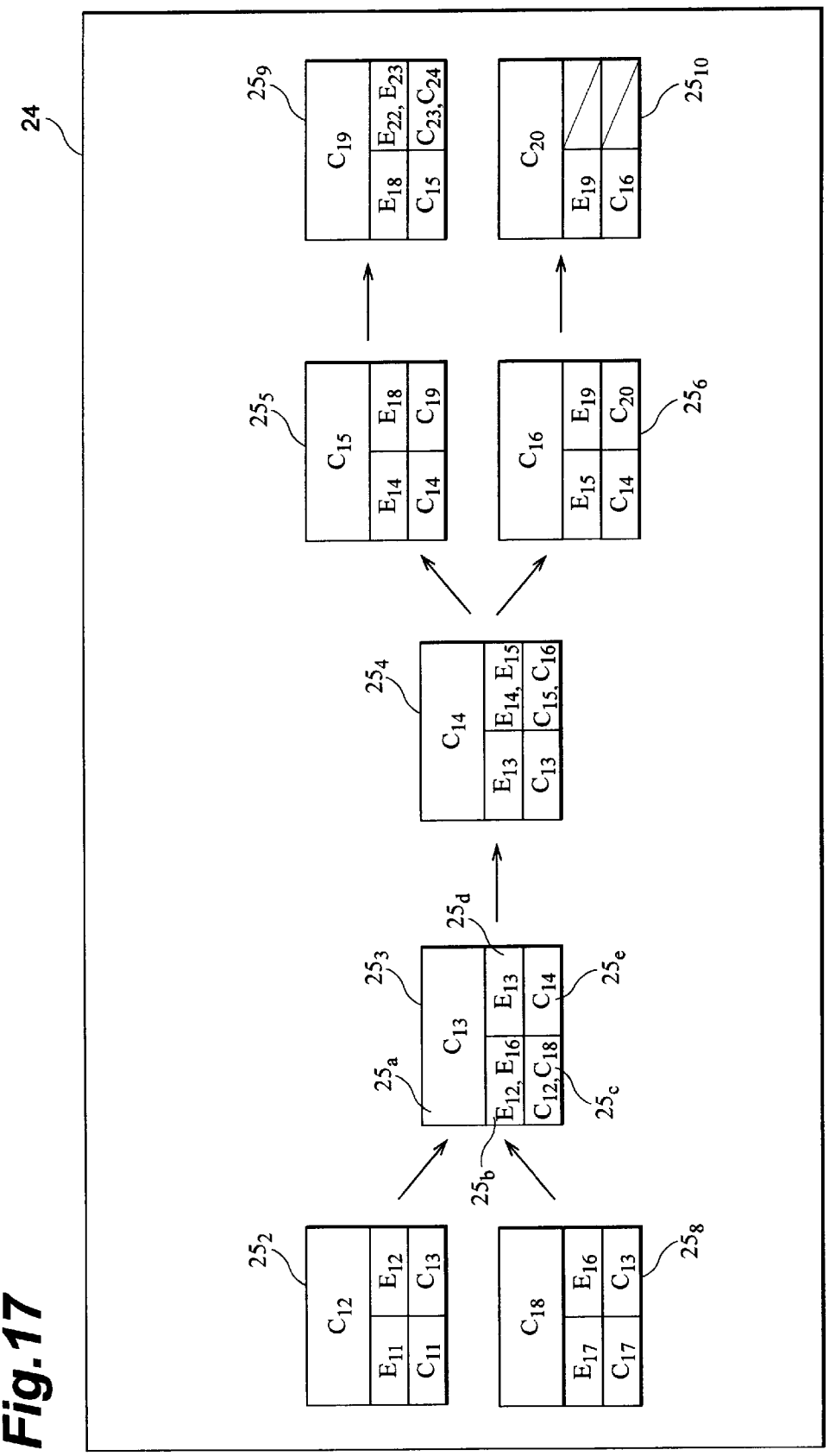
FIG. 17 is a drawing to show an example of internal structure of the reaction path information file (after scrolling) according to the present invention.

Next, the reaction path information file 24 is rewritten based on the calculation in S112 (S113). Specifically, first, the connection tables 25$_1$, 25$_7$ of the compounds having the maximum distance calculated in S112 (in the case of the example of FIG. 16, the compounds of the compound numbers $C_{11}$, $C_{17}$) are deleted from the reaction path information file 24. Namely, in the case of the example shown in FIG. 16, extracted are the compounds $C_{12}$ to $C_{16}$, $C_{18}$ whose number of reaction steps obtained is not more than 3 (a second predetermined number of reaction steps). Then reference is made to the connection tables 25$_5$, 25$_6$ (excluding the connection table 25$_7$ deleted) of the compounds accompanied by their adjacent reactions, obtained in S110, and new connection tables 25$_9$, 25$_{10}$ for the compounds stored in the member area 25*c* or in the member area 25*e* (in the case of the example of FIG. 16, the compounds of the compound numbers $C_{19}$, $C_{20}$) are prepared as shown in FIG. 17.

Figure 13:
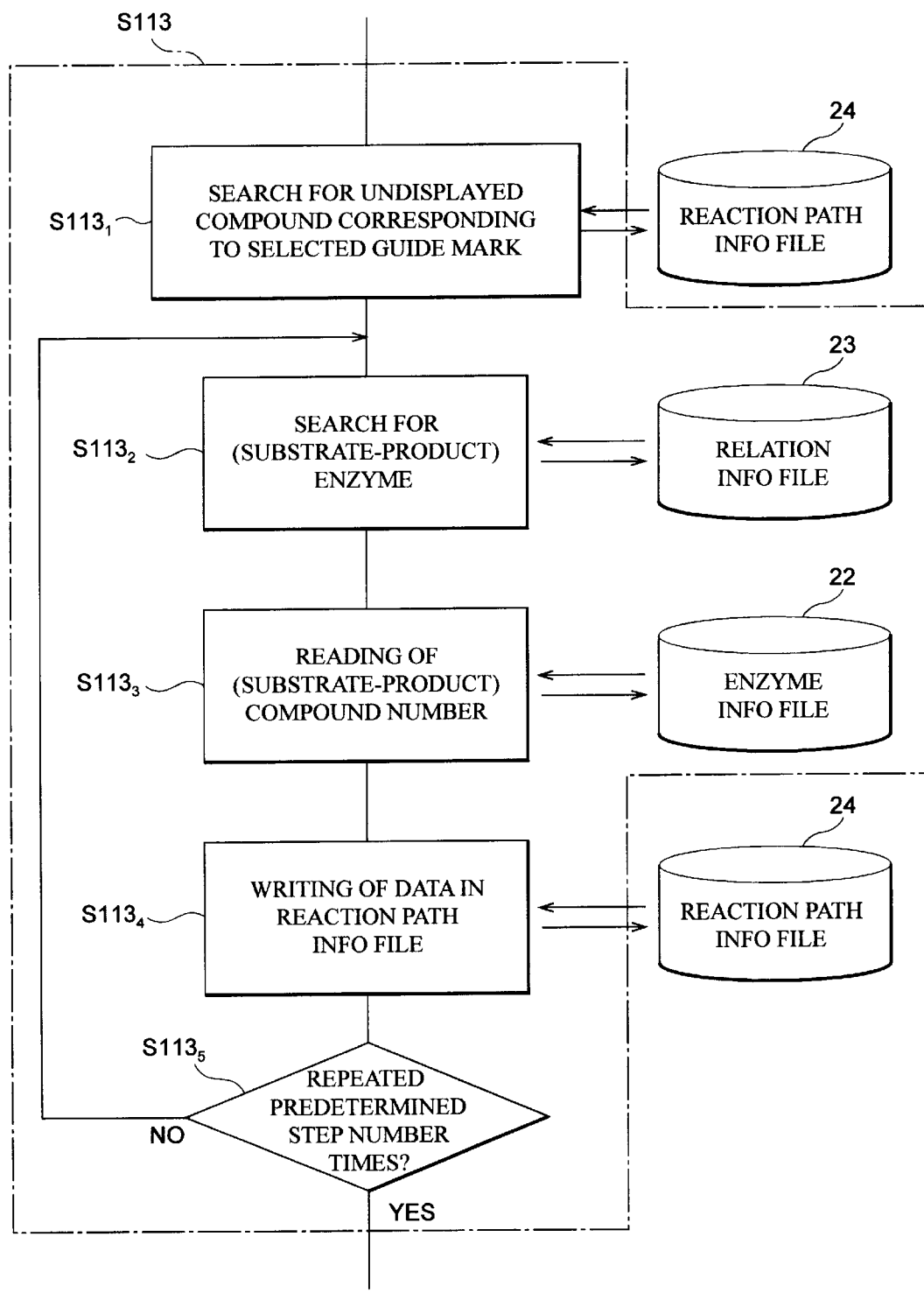
FIG. 13 is a flowchart to show the detailed process of S113 shown in FIG. 11.

Specifically, as shown in the flowchart of FIG. 13, the reaction path information file 24 is searched for the undisplayed compound $C_{19}$ that is not displayed on the display 30, out of the compounds $C_{15}$, $C_{19}$ constituting the undisplayed, adjacent reaction a indicated by the selected guide mark (S113$_1$) and the relation information file 23 is referenced to read an enzyme number of an enzyme for which the undisplayed compound $C_{19}$ is a substrate and an enzyme number of an enzyme by which the undisplayed compound $C_{19}$ is a product, out of the file (S113$_2$). Further, based on each of the enzyme numbers read in S113$_2$, a compound number of a compound as a substrate for this enzyme and a compound number of a compound as a product by this enzyme are read from the enzyme information file 22 (S113$_3$). Then the compound number read in S113$_1$, the enzyme numbers read in S113$_2$, and the compound numbers read in S113$_3$ are successively written in the form of a new connection table 25$_9$, 25$_{10}$ in the reaction path information file 24 (S113$_4$).

Figure 18:
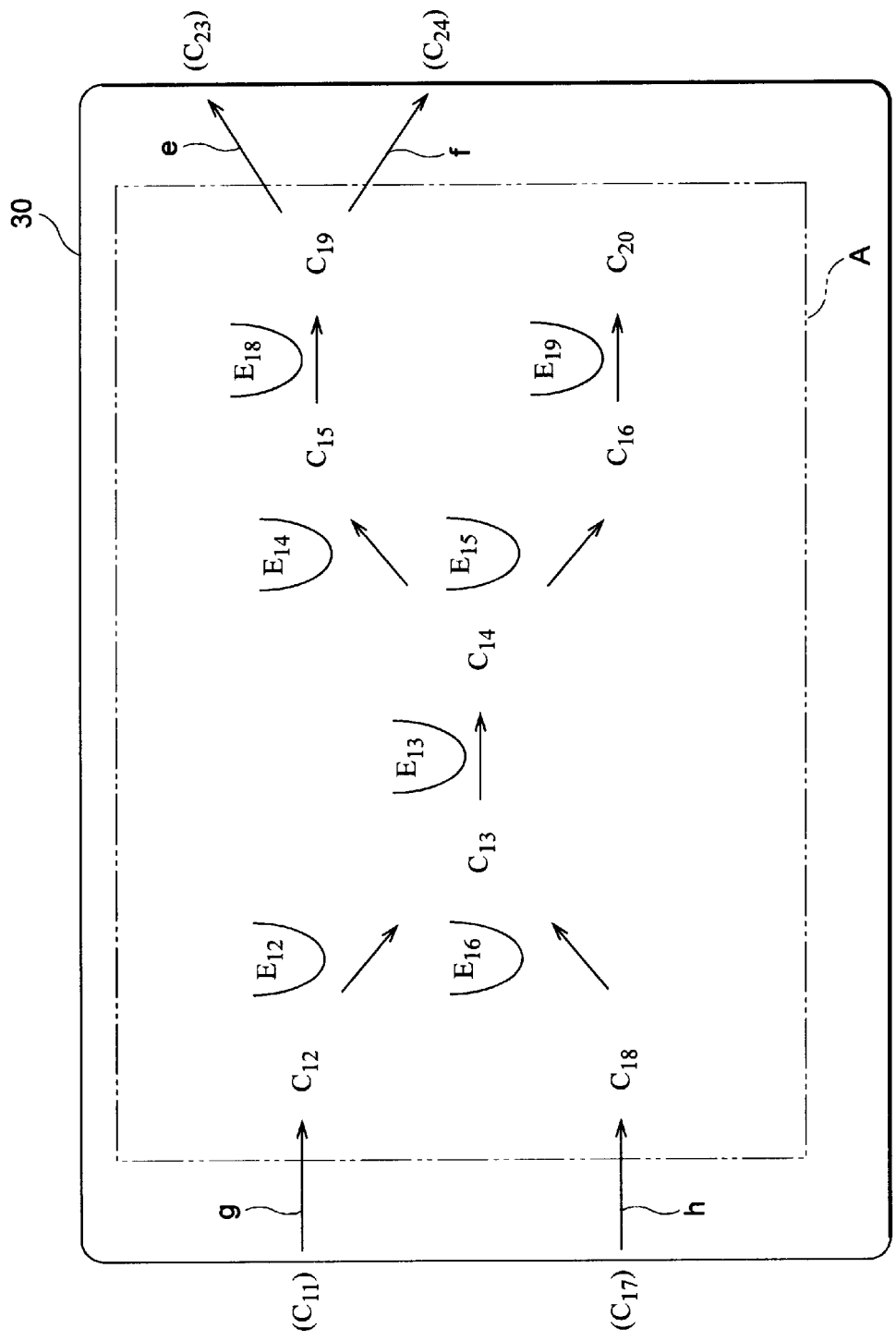
FIG. 18 is a drawing to show a display example of the reaction path diagram (after scrolling) according to the present invention, on the display.

Then the process is returned to S108 to prepare a new reaction path diagram, based on the reaction path information file 24 rewritten in S113. This new reaction path diagram is displayed over the old reaction path diagram already displayed on the display 30. As a result, the reaction path diagram on the display 30 is scrolled by one reaction step, as shown in FIG. 18. In this way, the reaction path diagram is scrolled so as to display the undisplayed compounds $C_{19}$, $C_{20}$ obtained in S113 on the display 30 while displaying the compounds $C_{12}$ to $C_{16}$, $C_{18}$ extracted in S112 on the display 30 (scrolling is done from the reaction path diagram shown in FIG. 15 to the reaction path diagram shown in FIG. 18).

The above scrolling may be done instantaneously by switching of screen; or, the reaction path diagram may be moved smoothly, using the known image processing technology. Further, this scrolling may be done by moving the reaction path diagram stepwise. The above processes of S108 to S113 are carried out every selection of guide mark in Sill and the reaction path diagram indicated on the display 30 is scrolled by one reaction step every selection of guide mark.

The operator is allowed to preliminarily set the number of scroll steps for scrolling of reaction path diagram. The above embodiment is an example in which the number of scroll steps is "1." For example, when the number of scroll steps is set to "2," the process of S113 is carried out as follows. First, the connection tables $25_1$, $25_2$, $25_7$, $25_8$ for the compounds of the maximum distance and the compounds of the second largest distance are deleted. Then the processes of $S113_2$ to $S113_4$ are repeated as shown in FIG. 13 to prepare the connection tables $25_9$, $25_{10}$ for the above undisplayed compounds $C_{19}$, $C_{20}$ and connection tables (not illustrated) for compounds $C_{23}$, $C_{24}$ each forming an undisplayed, adjacent reaction with the compound $C_{19}$ or $C_{20}$. As a result of these processes, the reaction path diagram prepared in S108 is a diagram shifted by two reaction steps (not illustrated). In S109 this reaction path diagram is displayed on the display 30, whereby the reaction path diagram is scrolled by two reaction steps.

In the present invention the scrolling of the reaction path diagram displayed on the display 30 is made in the direction toward the undisplayed, adjacent reaction specified by the selected guide mark, and the scrolling is preferably carried out in such a state that the number of reaction steps displayed on the display means is kept at the predetermined number of reaction steps (the first predetermined number of reaction steps). From this point of view, the aforementioned scrolling is suitably carried out by several reaction steps at a time (while deleting several reaction steps and adding several reaction steps); preferably, stepwise by one reaction step at a time (while deleting one reaction step and adding one reaction step). Accordingly, the preferred relation is normally as described below among the first predetermined number of reaction steps, the second predetermined number of reaction steps, and the predetermined number of scroll steps described previously.

{(first predetermined-number of reaction steps)−(predetermined number of scroll steps)}=(second predetermined number of reaction steps)

It should be noted that the present invention is not limited to the above embodiment, but can involve a variety of modifications. For example, the reaction path diagram display program 12 prepared the reaction path diagram of several reaction steps before and after the center of the predetermined compound, but it may be modified to prepare a reaction path diagram of several steps in the reaction proceeding direction ahead the predetermined compound. The reaction path diagram display program 12 is also allowed to be arranged to prepare the reaction path diagram of several reaction steps in the opposite direction to the reaction proceeding direction from the predetermined compound.

The guide mark may be any mark that allows identification of a compound accompanied by an adjacent reaction; the background of this compound may be displayed by a different color from the other background; or indication of this compound may blink. The guide mark for indicating the direction of chemical reaction may be selected from those of various shapes, as well as the arrow a to arrow d described above. Specific examples of the guide mark are as follows.

⇁  ⇀  →  ➜  ⇒  >  ☞  ▷  ◇

Further, the selection of arrow a to arrow d in Sill may be done by pointing of arrow a to arrow d with an electronic pen; or by giving an input of an alpha-numeric letter for identification displayed near the arrow a to arrow d through the keyboard 50. Furthermore, the selection of arrow a to arrow d in Sill may be carried out by forming the arrow a to arrow d themselves in the form of a string of alpha-numeric letters for identification and typing the alpha-numeric letters through the keyboard 50.

Further, the reaction path diagram of enzyme reaction was explained in the present embodiment, but in a multi-step synthesis reaction path diagram the reaction path diagram can also be scrolled on the display 30 by the same processes.

Further, the reaction path information file 24 was produced during execution of the reaction path diagram display program 12 in the present embodiment; but in another conceivable arrangement the reaction path information preliminarily prepared is stored as the reaction path information file 24 in the second storage device 20 and the reaction path diagram is made and scrolled by use of the reaction path information file 24. In that case, the processes of S104 to S107 in the flowchart shown in FIG. 9 become unnecessary and the processes of $S113_2$ to $S113_5$ in the flowchart shown in FIG. 13 also become unnecessary.

In the above embodiment the reaction path information file 24 is rewritten in the process of S113 shown in FIG. 13. However, in the case where the reaction path information file 24 is divided into an area in which the reaction path information displayed on the display 30 is stored and an area in which the reaction path information not displayed is stored, the reaction path information file 24 does not have to be rewritten and only one thing necessary is to rewrite the reaction path information stored in the area in which the reaction path information displayed on the display 30 is stored.

INDUSTRIAL APPLICABILITY

As detailed above, the displaying method of reaction path diagram of compound according to the present invention displays the reaction path diagram of compound and the guide marks each indicating the undisplayed, adjacent reaction of end compound on the display means. When either one of the guide marks is selected, the reaction path diagram is scrolled along the reaction path to display an undisplayed compound (a compound as a starting material or as a product) making an undisplayed, adjacent reaction indicated by this guide mark on the display means. Accordingly, a series of reaction path diagrams can be displayed in succession on the display means by selecting the guide marks in order, whereby the method achieves an efficient search for a reaction path of a compound.

What is claimed is:

1. A method for displaying a reaction path diagram of compound by use of an apparatus comprising input means, display means, and storage means storing at least reaction path information about compounds in the form of a reaction path information file, said displaying method of reaction path diagram of compound comprising;

a step of searching said reaction path information file, based on data accepted by said input means, to prepare a reaction path diagram having a first predetermined number of reaction steps, and displaying said reaction path diagram on said display means, a step of extracting every end compound that is located at the end of the diagram, from compounds constituting the reaction path diagram displayed on said displaying means, searching said reaction path information file to extract an end compound accompanied by an undisplayed, adjacent reaction that is an adjacent reaction thereto and is not displayed on said display means, from said every end compound, and displaying on said display means a guide mark corresponding to the undisplayed, adjacent reaction in relation to the end compound accompanied by the undisplayed, adjacent reaction, and a step of, when said guide mark is selected, searching said reaction path information file for an undisplayed compound that makes the undisplayed, adjacent reaction indicated by the selected guide mark and is not displayed on said display means, and scrolling the reaction path diagram displayed on said display means so as to display said undisplayed compound on said display means.

2. The displaying method of reaction path diagram of compound according to claim 1, wherein said step of scrolling the reaction path diagram further comprises a step of obtaining a number of reaction steps from the end compound with respect to said end compound corresponding to said selected guide mark, for each of the compounds constituting the reaction path diagram displayed on said display means, and extracting a compound whose number of reaction steps obtained is not more than a second predetermined number of reaction steps, and wherein when scrolling said reaction path diagram, said undisplayed compound is displayed on said display means while displaying said extracted compound on the display means.

3. The displaying method of reaction path diagram of compound according to claim 1, wherein said guide mark is displayed near said end compound accompanied by the undisplayed, adjacent reaction.

4. The displaying method of reaction path diagram of compound according to claim 1, wherein said guide mark is a mark indicating direction of said undisplayed, adjacent reaction.

5. The displaying method of reaction path diagram of compound according to claim 1, wherein said reaction path diagram is scrolled according to a predetermined number of scrolling steps at a time.

6. A method for displaying a reaction path diagram of compound by use of an apparatus comprising input means, display means, and storage means;

wherein said storage means comprises a compound information file storing a list indicating a relation between compound numbers of compounds and canonical data corresponding to the respective compounds, and additional information about said compounds, an enzyme information file storing a list indicating a relation among enzyme numbers of enzymes, compound numbers of compounds as being substrates for said enzymes, and compound numbers of compounds as being products by said enzymes, and additional information about said enzymes, and a relation information file storing a list indicating a relation among compound numbers of compounds as keys, enzyme numbers of enzymes for which said compounds are substrates, and enzyme numbers of enzymes by which said compounds are products;

said displaying method of reaction path diagram of compound comprising;

a step of, when said input means accepts data about a compound, preparing said canonical data uniquely indicating a chemical structure of said compound from the data, further searching said compound information file based on the canonical data, and thereby reading a compound number of the compound corresponding to said canonical data if said canonical data exists in said compound information file, a step of reading an enzyme number of an enzyme for which the compound is a substrate and an enzyme number of an enzyme from which the compound is a product out of said relation information file, based on the compound number of the compound read in the foregoing step, a step of reading a compound number of a compound being a substrate for the enzyme and a compound number of a compound being a product by the enzyme out of said enzyme information file, based on the enzyme number of each of the enzymes read in the preceding step, a step of storing the compound numbers of the compounds and the enzyme numbers of the enzymes read in the foregoing steps, in said storage means in the form of a reaction path information file, a step of repeating the foregoing steps to prepare a reaction path diagram having a first predetermined number of reaction steps and displaying said reaction path diagram on said display means, a step of extracting every end compound that is located at the end of the diagram, from compounds constituting the reaction path diagram displayed on said display means, searching said reaction path information file to extract an end compound accompanied by an undisplayed, adjacent reaction that is an adjacent reaction thereto and is not displayed on said display means from said every end compound, and displaying on said display means a guide mark corresponding to the undisplayed, adjacent reaction in relation to the end compound accompanied by the undisplayed, adjacent reaction, and a step of, when the guide mark is selected, searching said reaction path information file for an undisplayed compound that makes the undisplayed, adjacent reaction indicated by the selected guide mark and is not displayed on said display means, and scrolling the reaction path diagram displayed on said display means so as to display said undisplayed compound on said display means.

7. The displaying method of reaction path diagram of compound according to claim 6, wherein said step of scrolling the reaction path diagram further comprises a step of obtaining a number of reaction steps from the end compound with respect to said end compound corresponding to said selected guide mark, for each of the compounds constituting the reaction path diagram displayed on said display means, and extracting a compound whose number of reaction steps obtained is not more than a second predetermined number of reaction steps, and wherein when scrolling said reaction path diagram, said undisplayed compound is displayed on said display means while displaying said extracted compound on the display means.

8. The displaying method of reaction path diagram of compound according to claim 6, wherein said step of scrolling the reaction path diagram further comprises a step of reading an enzyme number of an enzyme for which the undisplayed compound is a substrate and an enzyme number of an enzyme by which the undisplayed compound is a product out of said relation information file, based on the compound number of said undisplayed compound, a step of reading a compound number of a compound being a substrate for the enzyme and a compound number of a compound being a product by the enzyme out of said enzyme information file, based on the enzyme number of each of the enzymes read in the foregoing step, and a step of adding to said reaction path information file the compound numbers of the compounds and the enzyme numbers of the enzymes read in the foregoing steps.

9. The displaying method of reaction path diagram of compound according to claim 6, wherein said guide mark is displayed near said end compound accompanied by the undisplayed, adjacent reaction.

10. The displaying method of reaction path diagram of compound according to claim 6, wherein said guide mark is a mark indicating direction of said undisplayed, adjacent reaction.

11. The displaying method of reaction path diagram of compound according to claim 6, wherein said reaction path diagram is scrolled according to a predetermined number of scrolling steps at a time.

* * * * *